(12) United States Patent
Tateyama

(10) Patent No.: US 10,408,934 B2
(45) Date of Patent: Sep. 10, 2019

(54) OBJECT INFORMATION ACQUIRING APPARATUS

(71) Applicant: CANON KABUSHIKI KAISHA, Tokyo (JP)

(72) Inventor: Jiro Tateyama, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 127 days.

(21) Appl. No.: 15/235,255

(22) Filed: Aug. 12, 2016

(65) Prior Publication Data

US 2017/0052254 A1    Feb. 23, 2017

(30) Foreign Application Priority Data

Aug. 19, 2015 (JP) ................................ 2015-162132
Jun. 10, 2016 (JP) ................................ 2016-116259

(51) Int. Cl.
*A61B 5/00* (2006.01)
*G01S 15/89* (2006.01)
*G01S 7/52* (2006.01)

(52) U.S. Cl.
CPC ........ *G01S 15/8965* (2013.01); *A61B 5/0095* (2013.01); *G01S 15/8929* (2013.01); *G01S 15/8936* (2013.01); *G01S 15/8993* (2013.01); *G01S 15/8995* (2013.01); *G01S 7/52077* (2013.01); *G01S 15/8977* (2013.01)

(58) Field of Classification Search
CPC .................................................. A61B 5/0095
See application file for complete search history.

(56) References Cited

U.S. PATENT DOCUMENTS

| 9,417,179 | B2* | 8/2016 | Wada | G01N 21/1702 |
| 2010/0285518 | A1* | 11/2010 | Viator | G01N 21/1702 435/29 |
| 2011/0230750 | A1 | 9/2011 | Tateyama | 600/407 |
| 2011/0306865 | A1* | 12/2011 | Thornton | A61B 5/0059 600/407 |
| 2013/0072798 | A1 | 3/2013 | Tateyama | 600/444 |

(Continued)

FOREIGN PATENT DOCUMENTS

JP    2012-179348    9/2012

OTHER PUBLICATIONS

L.V. Wang et al., "Photoacoustic Tomography: In Vivo Imaging from Organelles to Organs", *Science*, vol. 335, pp. 1458-1462 (Mar. 23, 2012).

(Continued)

*Primary Examiner* — Hovhannes Baghdasaryan
(74) *Attorney, Agent, or Firm* — Venable LLP

(57) ABSTRACT

An object information acquiring apparatus according to the present invention includes: a supporter which supports a plurality of conversion elements each converting a photoacoustic wave from an object into an electrical signal; an imager which acquires an image of the object; a scanner which changes a relative position between the object and the supporter; an acquirer which acquires first and second specific information of the inside of the object based on an electrical signal acquired at a first and second relative position between the object and the supporter; and a corrector which corrects a deviation between the first and the second specific information based on positional information of the object.

12 Claims, 13 Drawing Sheets

(56) References Cited

U.S. PATENT DOCUMENTS

| | | | | |
|---|---|---|---|---|
| 2013/0312526 A1 | 11/2013 | Oishi | ............................ | 73/620 |
| 2014/0086016 A1* | 3/2014 | Wada | ................... | A61B 5/0095 |
| | | | | 367/178 |
| 2014/0155727 A1* | 6/2014 | Nanaumi | ............. | A61B 8/4209 |
| | | | | 600/407 |
| 2015/0114125 A1* | 4/2015 | Tanaka | ................. | A61B 5/0095 |
| | | | | 73/632 |
| 2016/0109415 A1 | 4/2016 | Tateyama | ........... | G01N 29/4463 |

OTHER PUBLICATIONS

U.S. Appl. No. 15/155,446, filed May 16, 2016.

\* cited by examiner

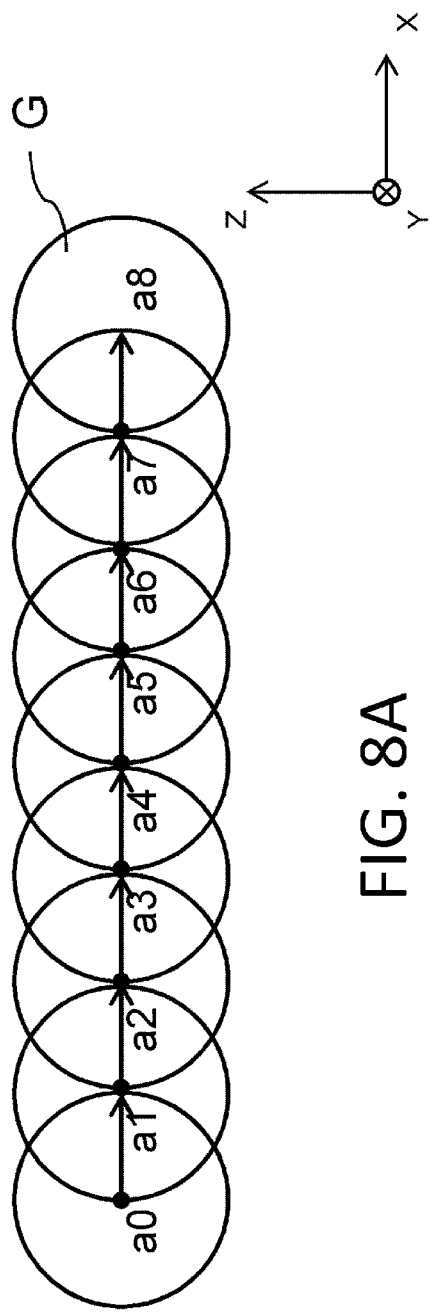
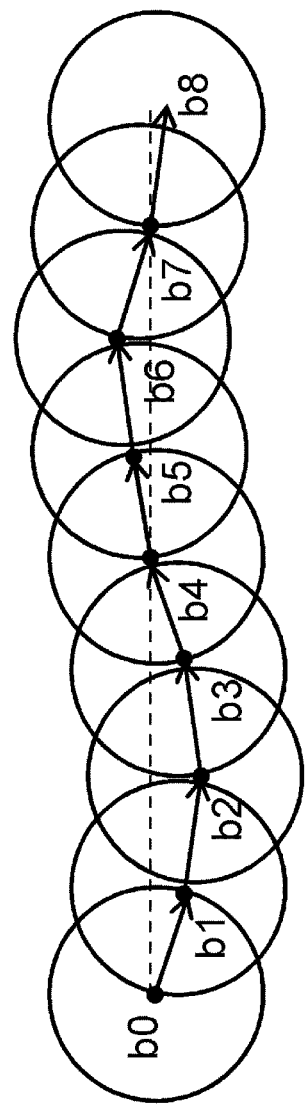
FIG. 8A
FIG. 8B

OBJECT INFORMATION ACQUIRING APPARATUS

BACKGROUND OF THE INVENTION

Field of the Invention

The present invention relates to an object information acquiring apparatus.

Description of the Related Art

Research on optical imaging apparatuses which irradiate an object such as a living organism with light from a light source such as a laser and converts information of the inside of the object obtained based on incident light into images is being actively pursued in the field of medicine. One optical imaging technique is photoacoustic imaging (PAI). In the photoacoustic imaging, an object is irradiated with pulsed light generated by a light source, a photoacoustic wave (generally, an ultrasonic wave) generated from tissue of the object having absorbed energy of the pulsed light propagated and diffused in the object is received, and imaging of object information is performed based on the received signal.

In photoacoustic imaging, in order to detect a difference in absorption rates of optical energy between an object part such as a tumor and other tissue, an elastic wave (a photoacoustic wave) generated as object tissue instantaneously expands when absorbing irradiated optical energy is received by a probe. By performing a process of mathematically analyzing the received signal, information of the inside of the object and, particularly, a distribution of initial sound pressure, a distribution of optical energy absorption density, a distribution of absorption coefficients, or the like can be acquired.

These pieces of information can also be used when quantitatively measuring a specific substance in an object such as oxygen saturation in blood. In recent years, preclinical research in which a blood vessel image of a small animal is imaged using photoacoustic imaging and clinical research in which the principle is applied to the diagnosis of breast cancer and the like are being actively pursued (see "Photoacoustic Tomography: In Vivo Imaging From Organelles to Organs", Lihong V. Wang, Song Hu, Science 335, 1458 (2012)).

Japanese Patent Application Laid-open No. 2012-179348 describes a photoacoustic apparatus which performs photoacoustic imaging using a probe in which an acoustic sensor is arranged on a hemisphere. Since this probe is capable of receiving a photoacoustic wave generated in a specific region (a high sensitivity region) at high sensitivity, resolution of object information in the specific region also increases. In addition, Japanese Patent Application Laid-open No. 2012-179348 describes scanning the probe in a given plane and then moving the probe in a direction perpendicular to the scanned plane and scanning in another plane, and performing such scans a plurality of times. Due to the scanning method described in Japanese Patent Application Laid-open No. 2012-179348, functional information of an object with high resolution can be acquired in a wide range.

Patent Literature 1: Japanese Patent Application Laid-open No. 2012-179348
Non Patent Literature 1: "Photoacoustic Tomography: In Vivo Imaging from Organelles to Organs", Lihong V. Wang, Song Hu, Science 335, 1458 (2012)

SUMMARY OF THE INVENTION

However, when the object is a living organism, body motion occurs due to breathing and the like. When body motion occurs in the scanning method described in Japanese Patent Application Laid-open No. 2012-179348, a relative positional relationship between the object and a probe deviates from an expected relationship while the probe is in motion. As a result, accuracy of reconstruction may be affected. In particular, when body motion occurs in a case where volume information is obtained by connecting respective high sensitivity regions produced by a plurality of scans in order to obtain high-resolution functional information of an object over a wide range, a deviation of positions occurs where the high sensitivity regions are connected to each other and resolutions in these portions decline. A similar problem arises when a shape of the object changes due to causes other than body motion.

The present invention has been made in consideration of the problems described above. An object of the present invention is to provide a technique that enables specific information of an object to be acquired with accuracy even when a shape of the object changes while photoacoustic imaging is being performed.

The present invention provides an object information acquiring apparatus, comprising:
a light source which generates light;
a plurality of conversion elements each receiving an acoustic wave generated when an object is irradiated with the light, and outputting an electrical signal;
a supporter which supports the plurality of conversion elements;
an imager which is provided on the supporter and which acquires an image of the object;
a scanner which changes a relative position between the object and the supporter;
a specific information acquirer which acquires first specific information of the inside of the object based on an electrical signal acquired at a first relative position between the object and the supporter, and which acquires second specific information of the inside of the object based on an electrical signal acquired at a second relative position between the object and the supporter that differs from the first relative position; and
a corrector which corrects a deviation of positions inside the object between the first specific information and the second specific information based on positional information of the object.

The present invention also provides an object information acquiring apparatus, comprising:
a light source which generates light;
a plurality of conversion elements each receiving an acoustic wave generated when an object is irradiated with the light, and outputting an electrical signal;
a supporter which supports the plurality of conversion elements and which is arranged at a distance from the object;
an imager which is provided on the supporter and which acquires an image of an external appearance of the object;
a scanner which performs scanning that changes a relative position between the object and the supporter;

a positional information acquirer which acquires, at a plurality of the relative positions during the scanning, positional information of the object based on the image acquired by the imager; and a specific information acquirer which acquires specific information of the inside of the object based on the electrical signal and the positional information.

According to the present invention, a technique can be provided which enables specific information of an object to be acquired with accuracy even when a shape of the object changes while photoacoustic imaging is being performed.

Further features of the present invention will become apparent from the following description of exemplary embodiments with reference to the attached drawings.

BRIEF DESCRIPTION OF THE DRAWINGS

FIGS. 8A and 8B are diagrams showing a transition of movement of the high sensitivity region G in an XZ plane;

DESCRIPTION OF THE EMBODIMENTS

Figure 1:
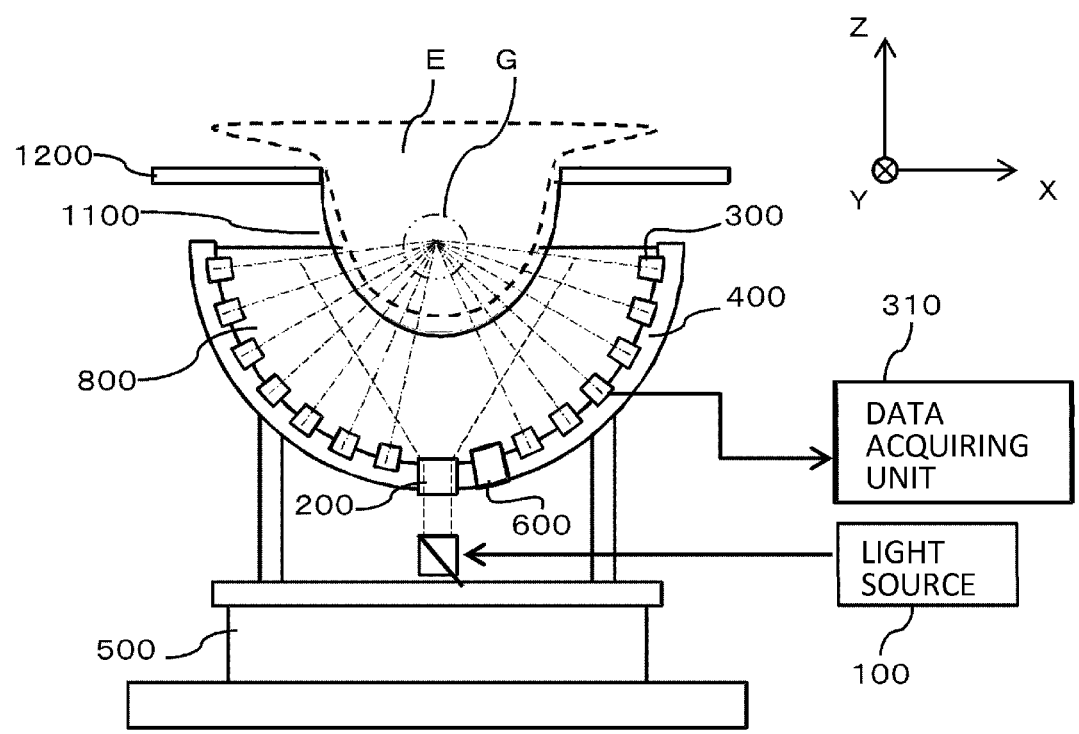
FIG. 1 shows a configuration of a photoacoustic apparatus according to the present invention.

Hereinafter, a preferred embodiment of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the description presented below.

The present invention relates to a technique for detecting an acoustic wave propagating from an object and generating and acquiring specific information of the inside of the object. Accordingly, the present invention can be considered an object information acquiring apparatus or a control method thereof, or an object information acquiring method and a signal processing method. The present invention can also be considered a program that causes an information processing apparatus including hardware resources such as a CPU and a memory to execute these methods or a storage medium storing the program.

The object information acquiring apparatus according to the present invention includes an apparatus (a photoacoustic apparatus) utilizing a photoacoustic effect in which an acoustic wave generated inside an object by irradiating the object with light (an electromagnetic wave) is received and specific information of the object is acquired as image data. Specific information acquired according to the present invention is a value reflecting an absorption rate of optical energy. For example, a generation source of acoustic waves generated by light irradiation, initial sound pressure inside an object, optical energy absorption density or an optical energy absorption coefficient derived from initial sound pressure, and the like can be considered "specific information based on light absorption" or "optical characteristic values of the inside of an object". Specific information also includes concentration-related information of substances constituting tissue and is also referred to as functional information.

Concentration-related information includes a value related to concentration of a substance present inside an object which is obtained using specific information based on light absorption corresponding to a plurality of wavelengths. Specific examples include oxygen saturation, a value obtained by weighting oxygen saturation with intensity of an absorption coefficient or the like, total hemoglobin concentration, oxyhemoglobin concentration, and deoxyhemoglobin concentration. In addition, concentration-related information may be glucose concentration, collagen concentration, melanin concentration, or a volume fraction of fat or water. Furthermore, a two-dimensional or three-dimensional specific information distribution is obtained based on concentration-related information at each position inside the object. Distribution data may be generated as image data. A distribution related to an optical characteristic value or a distribution of concentration-related information is a specific information value distribution.

The object information acquiring apparatus according to the present invention includes an ultrasonic echo apparatus which transmits an acoustic wave to an object, receives an acoustic wave (an echo wave) reflected by a surface or interior of the object, and acquires specific information of the object as image data. The specific information in this case is information reflecting an acoustic impedance inside the object and is also referred to as morphological information.

An acoustic wave according to the present invention is typically an ultrasonic wave and includes an elastic wave which is also referred to as a sonic wave or an acoustic wave. An electrical signal converted from an acoustic wave by a probe or the like is also referred to as an acoustic signal. However, descriptions of an ultrasonic wave and an acoustic wave in the present specification are not intended to limit a wavelength of such elastic waves. An acoustic wave generated by a photoacoustic effect is referred to as a photoacoustic wave or an optical ultrasonic wave. An electrical signal derived from a photoacoustic wave is also referred to as a photoacoustic signal.

Primary objects of the photoacoustic apparatuses according to the embodiment presented below are to diagnose a malignant tumor, a vascular disease, and the like, perform a follow-up observation of chemotherapy, and the like with respect to a human or an animal. Therefore, an object is assumed to be a part of a living organism or, more specifically, a part of a human or an animal (such as a breast, an organ, the circulatory system, the digestive system, a bone, a muscle, and fat). Substances that are inspection objects include hemoglobin, glucose, water present in the body, melanin, collagen, and lipids. Furthermore, any substance with a characteristic light absorption spectrum including contrast agents such as indocyanine green (ICG) administered into the body may suffice as an inspection object.

First Practical Example

<Basic Configuration>

Figure 2:
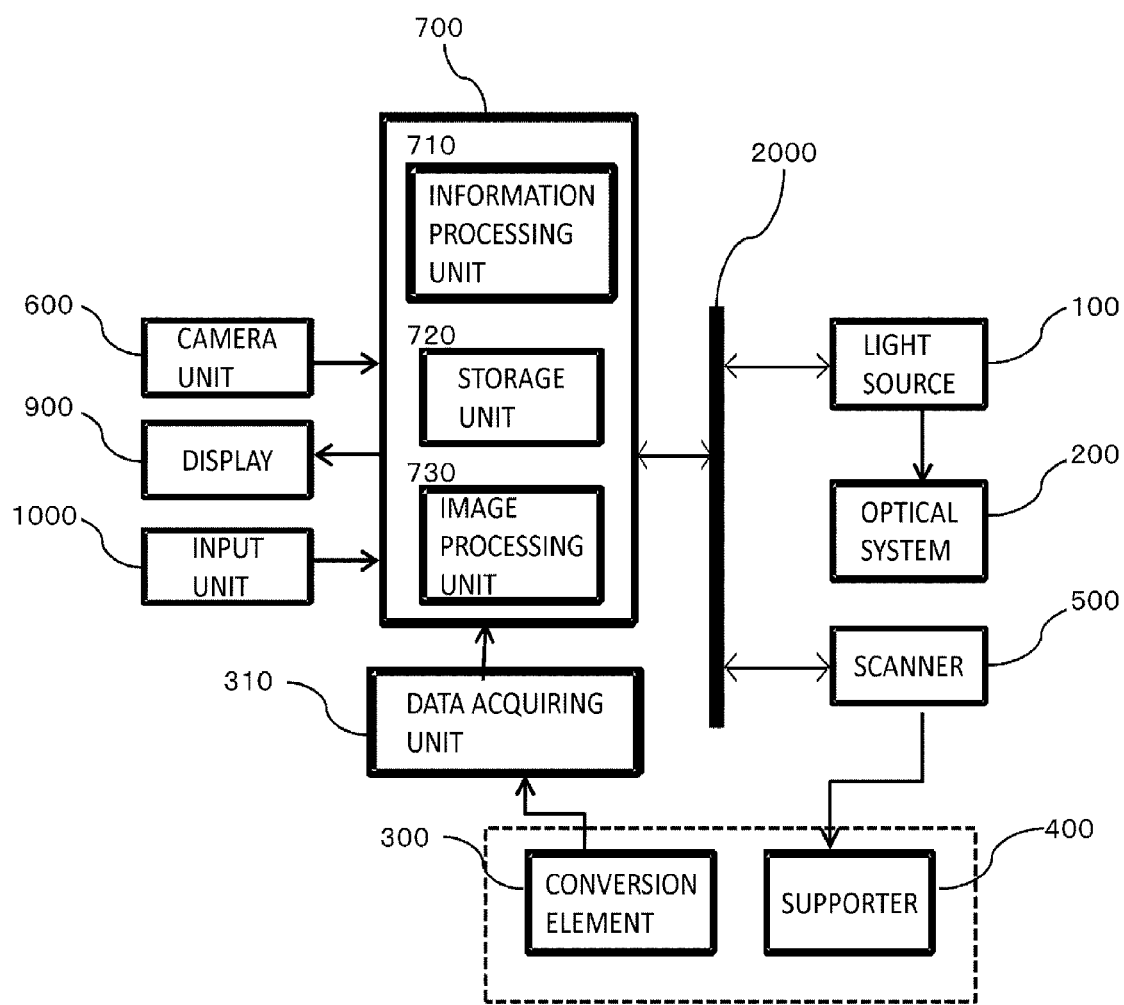
FIG. 2 shows a connection of a photoacoustic apparatus according to the present invention.

FIG. 1 is a schematic view of a photoacoustic apparatus according to the present practical example. This apparatus acquires information (functional information) such as optical characteristics of an object E based on a received signal of a photoacoustic wave generated by a photoacoustic effect. In addition, FIG. 2 is a diagram showing an internal configuration of the photoacoustic apparatus according to the present practical example. As shown in FIGS. 1 and 2, as basic components, the apparatus includes a light source 100, an optical system 200, a conversion element 300, a data acquiring unit 310, a supporter 400, a scanner 500, a camera unit 600, and an information processing apparatus 700. The apparatus may further include a display 900 as a display unit, an input unit 1000, a shape holding unit 1100, and a mounting unit 1200. Hereinafter, respective components of the photoacoustic apparatus and a configuration used for measurement will be described.

(Object)

Examples of the object E that is an object of measurement include a part of a living organism such as a breast or a limb and a phantom which is used for apparatus adjustment and which simulates acoustic characteristics and optical characteristics of a living organism. Acoustic characteristics specifically refer to a propagation speed and an attenuation rate of an acoustic wave. Optical characteristics specifically refer to an absorption coefficient and a scattering coefficient of light. In the case of a living organism, light absorbers with large light absorption coefficients in the object E include hemoglobin, water, melanin, collagen, and lipids. With a phantom, a substance simulating optical characteristics is included in the phantom as a light absorber. Moreover, the object E is depicted by a dashed line in FIG. 1 for the sake of convenience.

(Light Source)

The light source 100 is an apparatus that generates pulsed light. A laser is desirable as the light source in order to obtain a large output. However, a flash lamp or a light-emitting diode may be used instead. In order to effectively generate a photoacoustic wave, light must be irradiated in a sufficiently short period of time in accordance with thermal characteristics of the object E. When the object E is a living organism, a pulse width of the pulsed light is desirably set to or below several ten nanoseconds. In addition, a near infrared region with a wavelength of around 700 to 1200 nm which is commonly referred to as a biological window is desirable as a wavelength of the pulsed light. Since light in this region reaches relatively deep portions of a living organism, specific information of deep portions can be acquired. When limited to measurement of surface portions of a living organism, a region from visible light to near infrared light with a wavelength of around 500 to 700 nm may also be used. Furthermore, desirably, an observation object has a high absorption coefficient with respect to the wavelength of the pulsed light.

(Optical System)

The optical system 200 is an apparatus which changes a shape or light density of the pulsed light generated by the light source 100 so as to acquire a desired light distribution and guides the pulsed light to the object E. Specifically, the optical system 200 can be constituted by optical devices such as an optical fiber, a mirror, a lens, a prism, and a diffuser plate. In the present practical example, the optical system 200 is configured so as to illuminate a region of a center of curvature of a hemispherical supporter.

In addition, a maximum permissible exposure (MPE) is set with respect to intensity of light that is permitted to irradiate living tissue by the following safety standards. (IEC 60825-1: Safety of laser products, JIS C 6802: Safety Standards for Laser Products, FDA: 21CFR Part 1040.10, ANSI Z136.1: Laser Safety Standards, and the like)

Maximum permissible exposure defines the intensity of light that can be irradiated per unit area. Therefore, by collectively irradiating a large area of the surface of the object E, a large amount of light can be guided to the object E. As a result, a photoacoustic wave can be received at a high SN ratio. Therefore, favorably, light is spread over a relatively wide area as depicted by a dashed line in FIG. 1 instead of focusing light using a lens.

(Conversion Element)

The conversion element 300 is an element which receives a photoacoustic wave and converts the photoacoustic wave into an electrical signal. A conversion element with a high receiving sensitivity and a wide frequency band with respect to photoacoustic waves from the object E is desirable. As a member constituting the conversion element 300, a piezoelectric ceramic material represented by lead zirconate titanate (PZT), a polymer piezoelectric film material represented by polyvinylidene fluoride (PVDF), and the like can be used. Alternatively, an element other than a piezoelectric element may be used. For example, a capacitance-type element such as a capacitive micro-machined ultrasonic transducer (a cMUT), a conversion element using a Fabry-Perot interferometer, and the like can be used.

Figure 3:
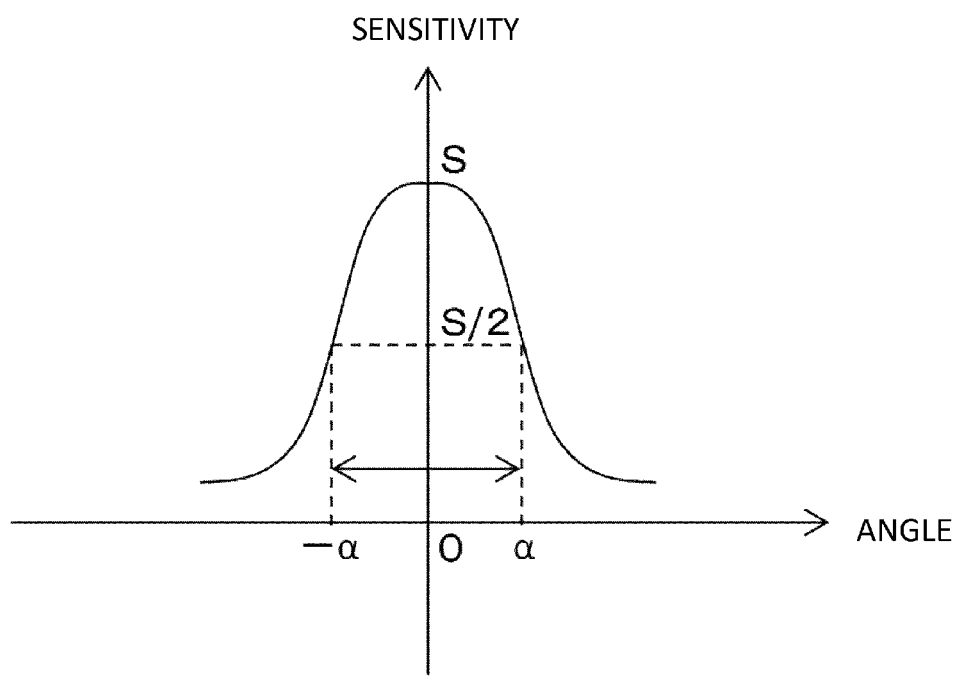
FIG. 3 is a diagram showing sensitivity characteristics of a conversion element.

FIG. 3 shows an example of receiving sensitivity characteristics of the conversion element 300. A horizontal axis represents an angle of incidence formed between a normal direction of a receiving surface of the conversion element 300 and a direction of incident of a photoacoustic wave. A vertical axis represents receiving sensitivity characteristics per angle. In the example shown in FIG. 3, receiving sensitivity is highest in a case of incidence from the normal direction of the receiving surface and the larger the angle of incidence, the lower the receiving sensitivity. Moreover, while the conversion element 300 according to the present practical example has a receiving surface with a circular planar shape, a shape of the receiving surface is not limited thereto.

In addition, an angle of incidence when receiving sensitivity equals half S/2 of a maximum value S is denoted by α. In the present practical example, a region where a photoacoustic wave enters at an angle of incidence of α or smaller to the receiving surface of the conversion element 300 is assumed to be a receiving region capable of reception at high sensitivity. In FIG. 1, a direction with highest receiving sensitivity (a directional axis) of each conversion element 300 is depicted by a dot chain line.

Moreover, the data acquiring unit 310 constituted by an A/D converter and a logic circuit such as an FPGA or an ASIC is connected to the conversion element 300. An electrical signal obtained by receiving a photoacoustic wave via the conversion element 300 is converted into digital data using the A/D converter of the data acquiring unit 310 and data transmission is performed from the logic circuit to the information processing apparatus 700. In addition, an amplifier which amplifies signal strength is also favorably provided.

(Supporter)

Figure 4:
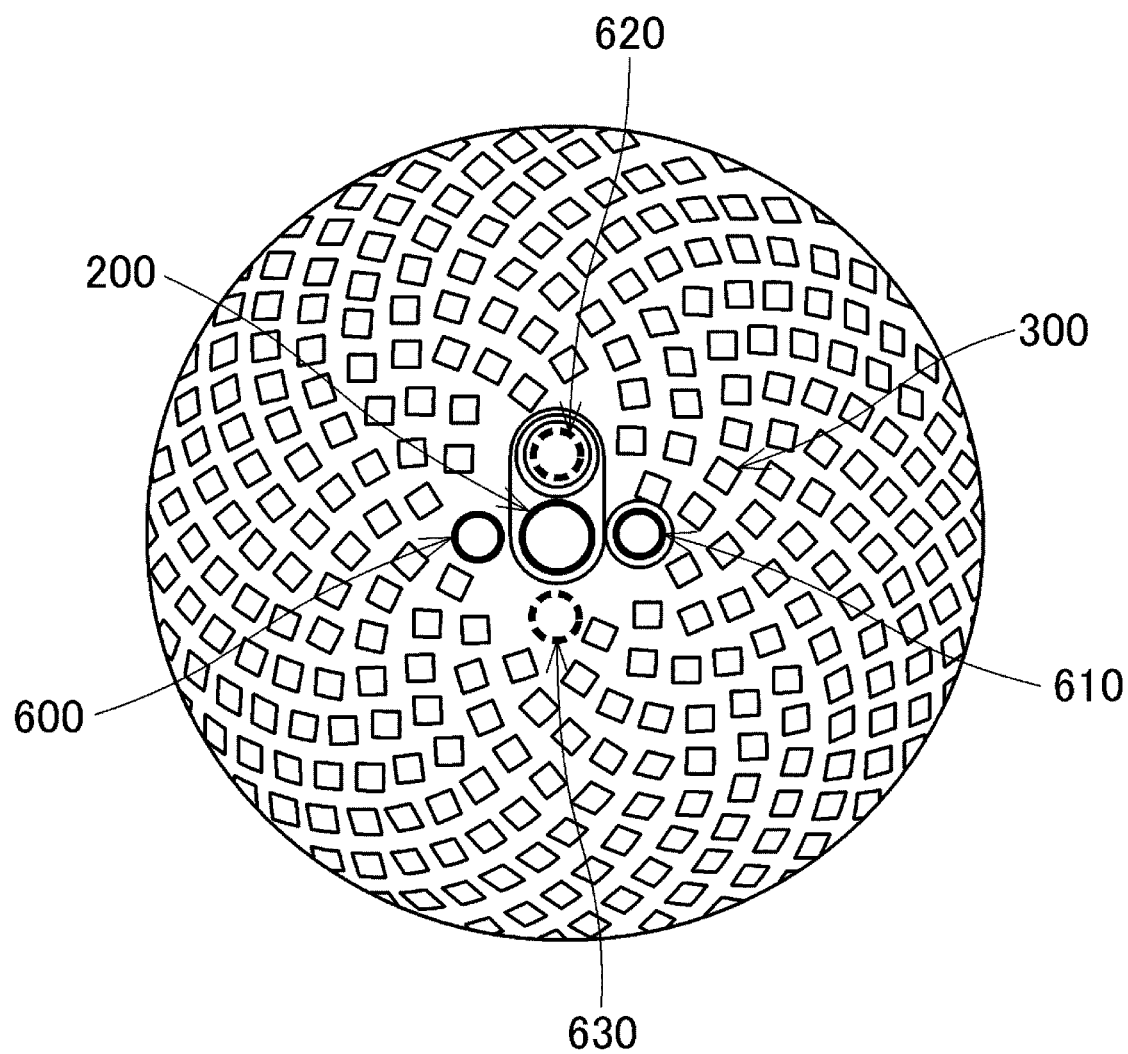
FIG. 4 is a top view of a supporter 400.

FIG. 4 is a top view of the supporter 400. The supporter 400 according to the present practical example is a hemispherical container with a shape obtained by splitting a sphere in half. A center portion of the circle protrudes in a depth direction with respect to the paper plane. A plurality of conversion elements 300 are installed on an inside surface of the supporter 400, and the optical system 200 which irradiates the object E with pulsed light and the camera unit 600 which is an imager that captures an image of an external appearance of the object E are installed at a center of a bottom section of the supporter 400. Furthermore, the inside of the supporter 400 is filled with an acoustic matching member 800 to be described later. The supporter 400 is favorably constructed using a metal material or the like with high mechanical strength in order to support these members.

The plurality of conversion elements 300 are arranged on a hemispherical surface so that a receiving direction (a directional axis) of each of the plurality of conversion elements 300 provided in the supporter 400 is oriented toward a center of curvature of the hemisphere. FIG. 1 is a sectional view of the hemispherical supporter 400 as cut along a central axis. Receiving directions (dot chain lines) of the conversion elements 300 converge in a partial region (G) of the object E. Due to such an element arrangement, a photoacoustic wave generated near the center of curvature of the supporter 400 can be received at higher sensitivity.

When the plurality of conversion elements 300 are hemispherically arranged in this manner, functional information of the object E obtained using received signals by a method to be described later has high resolution at the center of curvature of the hemisphere and the further away from the center, the lower the resolution. The high sensitivity region G according to the present practical example indicates a region from a point with highest resolution to a point with half resolution of the highest resolution. A region enclosed by a two-dot chain line in FIG. 1 corresponds to this region and is defined as the high sensitivity region G. Moreover, an arrangement of the plurality of conversion elements 300 is not limited thereto. For example, directional axes of the plurality of conversion elements 300 need not necessarily intersect each other at a single point.

In addition, as a mounting pattern of the conversion elements 300 arranged on the hemispherical surface of the supporter 400, various mounting pattern such as a staggered array, a spiral array, a uniform array, and a random array are conceivable. FIG. 4 shows a pattern in which the conversion elements 300 are mounted at equal intervals along a plurality of spiral arrays. With such an arrangement, since the directional axes of the respective elements are all pointed towards the center of curvature of the hemisphere, even when one limited portion of the spherical surface is made a non-mounting region, resolution of the region G is not significantly affected.

In the present practical example, as shown in FIG. 4, conversion elements 300 are not mounted in a vicinity of a pole of the bottom section of the supporter 400 and, instead, the optical system 200 and the camera units 600 and 610 are collectively arranged. This serves the purposes of equally irradiating the object E with light and photographing an entire image of the object E with the camera units. However, arrangements of the cameras and the like are not limited thereto. According to the arrangement shown in FIG. 4, a concentric area centered on the pole can be secured. In other words, when the optical system 200 is arranged on the pole, a concentric space centered on the optical system 200 can be secured. Therefore, the two camera units 600 and 610 are installed at positions on opposite sides of the optical system 200.

Moreover, when installing camera units at three or more locations, the camera units are desirably equally arranged with the pole of the hemispherical shape at center. For example, when the conversion elements 300 are arranged using four spiral arrays, there are regions in a central section of the hemispherical supporter 400 where conversion elements are not mounted in four directions. For example, the optical system 200 that performs light irradiation may be arranged in the central section, cameras may be mounted in two of the regions where conversion elements are not mounted in four directions, and holes of a matching liquid supply and discharge system and a temperature sensor for monitoring temperature of the matching liquid may be respectively mounted in the remaining two regions. Positions denoted by the reference numerals 620 and 630 may be considered candidates when arranging these components.

When the conversion elements 300 are arranged using n-number of spiral arrays, there are regions in a central section of the hemispherical supporter 400 where conversion elements are not mounted in n-number of directions. Cameras according to the present invention may be mounted in these regions where conversion elements are not mounted in n-number of directions. When the number n of spiral arrays increases, the number of regions where conversion elements are not mounted increases but an area of each region decreases. As a result, enough area to mount a camera can no longer be secured. Therefore, preferably, the number of spiral arrays is two or more and eight or less at the most.

Meanwhile, in order to enable a photoacoustic wave generated in the high sensitivity region G to be received with high sensitivity, a direction of highest receiving sensitivity of at least a part of the plurality of conversion elements 300 supported by the supporter 400 may be pointed toward the high sensitivity region G. In other words, at least a part of the plurality of conversion elements 300 may be arranged on the supporter 400 so as to be capable of receiving a photoacoustic wave generated in the high sensitivity region G with high sensitivity.

In addition, compared to a case where directions of highest receiving sensitivity of the plurality of conversion elements 300 are parallel to each other, the plurality of conversion elements 300 need only be arranged on the supporter 400 so that axes (directional axes) along the directions of highest receiving sensitivity of the plurality of conversion elements 300 converge. Furthermore, the plurality of conversion elements 300 may be arranged so that the receiving surfaces of the plurality of conversion elements 300 conform to the supporter 400. The shape of the supporter 400 is not limited to a hemispherical shape as in the present practical example and may be any shape as long as the plurality of conversion elements 300 can be arranged as described above.

A "curved surface" according to the present practical example includes curved surfaces other than a surface on a true sphere. Specifically, a curved surface according to the present practical example includes a surface having irregularities thereon which can be regarded as a curved surface and a surface on an ellipsoid (a shape which is obtained by expanding an ellipse into three dimensions and which has a surface constituted by a quadratic curve) that can be regarded as a curved surface. In addition, a supporter according to the present practical example may be a surface formed by connecting a plurality of flat surfaces.

As shown in FIG. 1, favorably, a plurality of conversion elements 300 are arranged so that the high sensitivity region G is formed at a position where the object E is expected to be positioned. Furthermore, when the shape holding unit 1100 which holds a shape of the object E is provided as shown in FIG. 1, a plurality of conversion elements 300 are desirably arranged so that a high sensitivity region is formed near the shape holding unit 1100.

(Scanner)

The scanner 500 is an apparatus which changes a relative positional relationship between the object E and the supporter 400 by moving a position of the supporter 400 in X, Y, and Z directions shown in FIG. 1. To this end, the scanner 500 is provided with a guiding mechanism (not shown) in the X, Y, and Z directions, a driving mechanism (not shown) in the X, Y, and Z directions, and a position sensor (not shown) which detects a position of the supporter 400 in the X, Y, and Z directions. For example, a relative positional relationship at a given point in time can be defined as a first relative position and a positional relationship at another point in time which differs from the first relative position can be defined as a second relative position.

As shown in FIG. 1, since the supporter 400 is loaded on the scanner 500, a linear guide or the like capable of bearing a large load is favorably used as the guiding mechanism. In addition, a lead screw mechanism, a linking mechanism, a gear mechanism, a hydraulic mechanism, or the like can be used as the driving mechanism. A motor or the like can be used to provide a driving force. Furthermore, for example, a potentiometer using an encoder, a variable resistor, and the like can be used as the position sensor.

Moreover, in the present invention, since changing relative positions of the object E and the supporter 400 may suffice, the object E may be moved while keeping the supporter 400 fixed. When moving the object E, a configuration is conceivable in which the object E is moved by moving a supporting unit (not shown) that supports the object E. Alternatively, both the object E and the supporter 400 may be moved.

In addition, while movement is desirably performed continuously, the movement may be performed by repeating a certain step. While the scanner 500 is desirably a motor-driven stage, a manually-controlled stage may be used instead. However, configurations are not limited to those described above and any configuration may be adopted as long as at least one of the object E and the supporter 400 is movable.

(Camera Unit)

The camera unit 600 is an imaging apparatus which acquires an image of an external appearance of the object E as an imager. Installing the camera unit 600 in a vicinity of a center of the bottom section of the supporter 400 is preferable for the purpose of photographing an entire image of the object E. Based on an image signal output from the camera unit 600, a captured image is generated by an image processing unit 730 of the information processing apparatus 700. As the camera unit 600, an apparatus capable of capturing an image of an external appearance in accordance with the object can be used in addition to ordinary optical imaging apparatuses. Alternatively, the camera unit 600 may be capable of photographing moving images.

In this case, it is also favorable to add a separate camera unit 610 at a diagonal position of the camera unit 600 with respect to the pole of the hemisphere. With a three-dimensional measurement technique such as a stereoscopic method using two images captured by the camera units 600 and 610 at different positions, shape information of the object E can be acquired with accuracy. In a stereoscopic method, an arbitrary region is matched between two images photographed by cameras at different positions. Subsequently, based on an obtained parallax, a difference can be measured using triangulation. In order to detect positional information of the object E using a stereoscopic method, mutually corresponding characteristics points (representing a same point on an object) must be obtained on two or more captured images photographed simultaneously at different positions and the characteristics points must be measured. As the characteristics points, for example, a marker using ink or a stamp, a characteristic structure on a living organism such as a mole or a nipple, and the like can be used. Positional information is obtained by comparing corresponding characteristics points between the images.

(Information Processing Apparatus)

The information processing apparatus 700 includes an information processing unit 710, a storage unit 720, and an image processing unit 730. The information processing unit 710 is typically constituted by a CPU that performs computational processing and the image processing unit 730 is constituted by a graphics processing unit (a GPU) that performs image processing or the like. Moreover, the information processing unit and the image processing unit are not limited to configurations having a single element or a circuit and may be constituted by a plurality of elements or circuits. In addition, respective processes performed by the information processing apparatus 700 may be executed by any element or circuit. The storage unit 720 is typically constituted by a storage medium such as a ROM, a RAM, and a hard disk. Moreover, the storage unit is not limited to a configuration having a single storage medium and may be constituted by a plurality of storage media. The information processing apparatus 700 may be configured as a single apparatus or may be configured such that a plurality of blocks are connected in a wired or wireless manner to operate in cooperation with each other.

With the information processing unit 710 and the image processing unit 730, by applying signal processing (image reconstruction) based on electrical signals output from a plurality of conversion elements 300, functional information of the object E can be generated. In addition, the information processing unit 710 as a controller is capable of controlling operations of the respective components that constitute the photoacoustic apparatus via a bus 2000. Furthermore, favorably, the information processing apparatus 700 is configured so as to be capable of simultaneously performing pipeline processing on a plurality of signals. Accordingly, a period of time required to generate functional information of the object E can be reduced.

Moreover, respective processes to be performed by the information processing apparatus 700 can be stored in the storage unit 720 as a program to be executed by the information processing unit 710. However, a nonvolatile recording medium is necessary for the storage unit 720 storing the program. Among functions executed by the information processing apparatus 700, portions related to the acquisition of positional information can be regarded as a positional information acquirer. Among functions executed by the information processing apparatus 700, portions related to the acquisition of specific information can be regarded as a specific information acquirer. When the specific information acquirer acquires specific information of the inside of the object based on an electrical signal acquired at the first relative position, the specific information can be defined as first specific information. When the specific information acquirer acquires specific information of the inside of the object based on an electrical signal acquired at the second relative position, the specific information can be defined as second specific information. Among functions executed by the information processing apparatus 700, portions related to correction based on positional information of a deviation of positions between first specific information and second specific information can be regarded as a corrector.

(Acoustic Matching Member)

The acoustic matching member 800 fills a space between the object E and the conversion elements 300 and acoustically couples the object E and the conversion elements 300 with each other. When using the shape holding unit 1100, the acoustic matching member 800 may be arranged in a space between the conversion elements 300 and the shape holding unit 1100 and in a space between the shape holding unit 1100 and the object E. The acoustic matching member 800 in the respective spaces may be of a same type or different types.

The acoustic matching member 800 is favorably a material with an acoustic impedance resembling those of the object E and the conversion elements 300. More favorably, the acoustic matching member 800 is a material with an acoustic impedance midway between those of the object E and the conversion elements 300. In addition, the acoustic matching member 800 is favorably a material which transmits pulsed light generated by the light source 100. Furthermore, the acoustic matching member 800 is favorably a liquid. Specifically, water, castor oil, an ultrasonic gel, and the like can be used as the acoustic matching member 800.

(Display)

The display 900 is an apparatus which displays functional information of the object E output from the information processing apparatus 700 as a distribution image or as numerical data of a high sensitivity region of interest. For example, a liquid crystal display, a plasma display, an organic EL display, an FED, and the like can be used. Moreover, the display 900 may be provided separately from the object information acquiring apparatus according to the present invention.

(Input Unit)

The input unit 1000 is an apparatus used by a user for inputting and selecting desired information to and from the information processing apparatus 700. As the input unit 1000, a keyboard, a mouse, a touch panel, a dial, a button, and the like can be used. When a touch panel is adopted as the input unit 1000, the touch panel may serve as both the display 900 and the input unit 1000.

(Shape Holding Unit)

The shape holding unit 1100 is a member for keeping a shape of the object E constant. The shape holding unit 1100 is mounted to the mounting unit 1200. Moreover, a plurality of replaceable shape holding units 1100 may be used in accordance with a shape and a size of the object E. In this case, the mounting unit 1200 is configured so that a plurality of shape holding units can be mounted to and detached from the mounting unit 1200.

When irradiating the object E with light via the shape holding unit 1100, the shape holding unit 1100 is favorably transparent with respect to irradiation light. For example, polymethylpentene, polyethylene terephthalate, and the like can be used as the material of the shape holding unit 1100. In addition, when the object E is a breast, in order to reduce deformation of the breast shape and maintain a constant shape, a spherical crown shape created by cutting a sphere at a given section, a cup shape, and the like are favorable as the shape of the shape holding unit 1100. Moreover, the shape of the shape holding unit 1100 can be designed as appropriate in accordance with a volume or a desired shape after holding of the object E.

<Operation of Photoacoustic Apparatus>

Next, operations up to acquiring positional information of the object E and generating functional information of the object E will be described using the flow chart shown in FIG. 5. Step S100 is a step of inserting the object E into the shape holding unit 1100. At this point, a space between the supporter 400 and the shape holding unit 1100 and a space between the shape holding unit 1100 and the object E are filled with the acoustic matching member 800.

When a volume of the object E is greater than a capacity of the shape holding unit 1100, since a contour of the object E can be regarded as being the same as a contour of the shape holding unit 1100, an effect of body motion of the living organism need not be taken into consideration. However, the volume of the object E has individual variability and when smaller than the capacity of the shape holding unit 1100, a gap filled with the acoustic matching member 800 is created. As a result, body motion of the living organism becomes an influencing factor. In particular, when used as an imaging apparatus for screening diagnosis or the like, since a large shape holding unit is to be provided in anticipation of various sizes of the object E, the influence of body motion cannot be avoided.

Step S200 is a step in which the scanner 500 moves the supporter 400 to a desired position within a movement region. The scanner 500 moves the supporter 400 to a first measurement position where measurement in the movement region is started. Positional information of the supporter 400 at the first measurement position is sent to the information processing apparatus 700 and stored as first measurement position information in the storage unit 720.

As the movement region at this point, a region enclosed by the shape holding unit 1100 holding the object E is desirably set. In other words, the information processing unit 710 as a region setting unit sets a movement region of the supporter 400 based on shape information of the shape holding unit 1100. Moreover, a technician or the like may set a region using the input unit 1000. In addition, at this point, input of various conditions related to measurement (measurement accuracy, measurement period, measurement object, a given optical coefficient, and the like) may be prompted in addition to a region.

Figure 6:
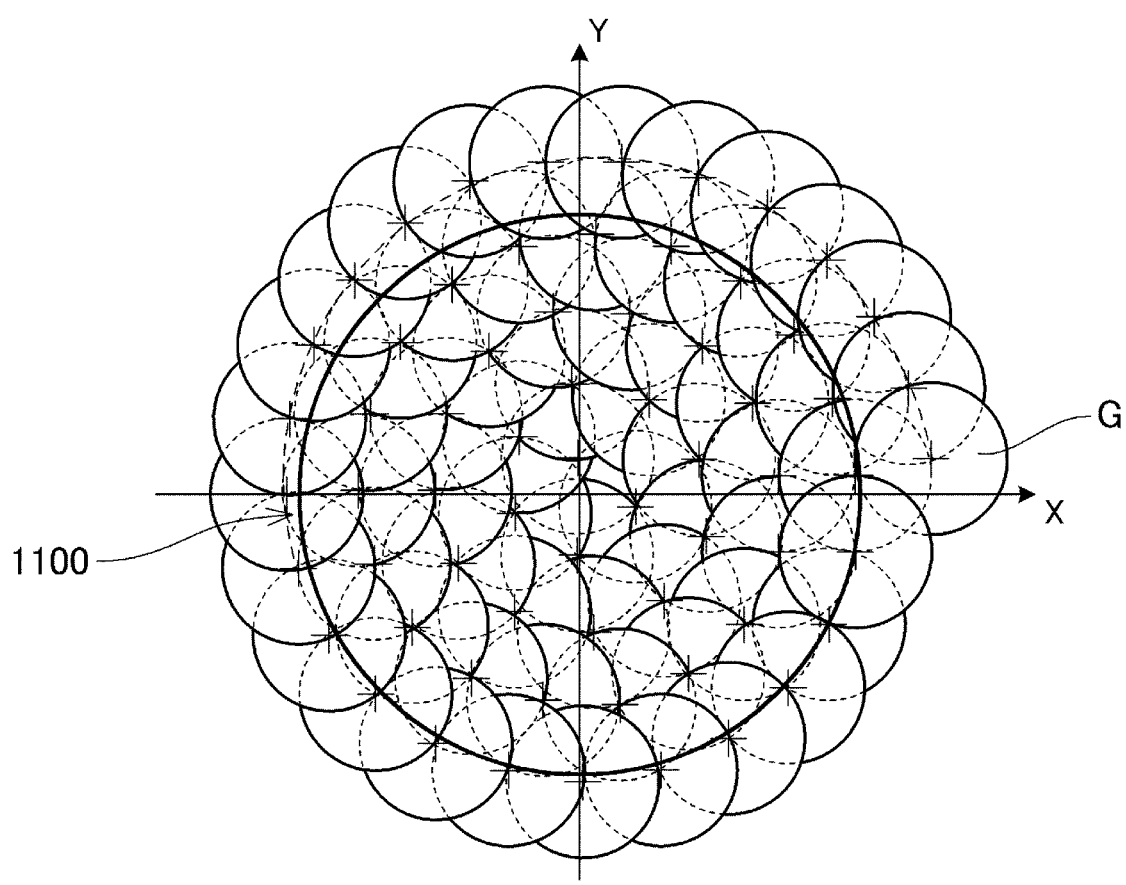
FIG. 6 is a diagram showing a movement region of a high sensitivity region G.

FIG. 6 shows a locus of movement of the high sensitivity region G accompanying scanning in comparison to a size of the shape holding unit 1100 as viewed from a vertical direction. As shown in FIG. 6, the information processing unit 710 sets a movement region of the supporter 400 in the X, Y, and Z directions so that the high sensitivity region G is formed inside the shape holding unit 1100. More favorably, the high sensitivity region G is formed inside the object. A position and a size of the high sensitivity region G are determined based on conditions such as an arrangement of the plurality of conversion elements 300 and a degree of required measurement accuracy. In consideration thereof, the information processing unit 710 sets the movement region so that the high sensitivity region G is formed inside the object based on shape information of the shape holding unit 1100 and information on the arrangement of the plurality of conversion elements 300 on the supporter 400.

Moreover, information on the size and position of the high sensitivity region G as determined based on the arrangement of the plurality of conversion elements 300 may be stored in the storage unit 720 in advance. In this case, the information processing unit 710 may set the movement region based on information on the size and position of the high sensitivity region G read from the storage unit 720 and shape information of the shape holding unit 1100.

In addition, the information processing unit 710 appropriately sets a measurement position of a photoacoustic wave inside the set movement region. The measurement position in this case is expressed as, for example, a position where light is irradiated during scanning or a position where an acoustic wave is received within a certain period of time following light irradiation. For example, the information processing unit 710 sets measurement positions at regular intervals in the movement region and controls driving of the light source 100 and the scanner 500.

Furthermore, driving of the light source 100 and the scanner 500 is favorably controlled so that the high sensitivity region G overlaps between measurement positions. In other words, since the high sensitivity region G has a spherical shape in the present practical example, pulsed light is favorably irradiated at least once before the supporter 400 moves a distance equal to a radius of the high sensitivity region G. This means that a received signal is acquired at least once while the supporter 400 moves a distance equal to the radius of the high sensitivity region G. The shorter the distance over which the supporter 400 is moved in a period from one light irradiation to a next light irradiation, the larger the overlapping region and the higher the S/N. However, in this case, since movement speed is low, more time is required by the measurement. Therefore, a movement speed and intervals of an acquisition period of received signals may be appropriately set in consideration of a desired S/N and measurement period.

Step S300 is a step of irradiating the object E with light from the light source 100 and detecting a generated photoacoustic wave with the plurality of conversion elements 300 to acquire a received signal. When the information processing unit 710 determines based on first measurement position information that the supporter 400 is at the first measurement position, the information processing unit 710 outputs a control signal so that the light source 100 generates light. The light is guided by the optical system 200 and irradiated on the object E via the acoustic matching member 800. Subsequently, light irradiated on the object E is absorbed inside the object E and a photoacoustic wave is generated.

The plurality of conversion elements 300 receive the photoacoustic wave generated inside the object E and propagated in the acoustic matching member 800 and converts the photoacoustic wave into an electrical signal as a received signal with the data acquiring unit 310. The electrical signal output from the data acquiring unit 310 is sent to the information processing apparatus 700 and is associated with the first measurement position information and stored in the storage unit 720 as an electrical signal at the first measurement position. Moreover, the received signal acquisition in the present step is not limited to a method of repetitively stopping and moving the supporter and acquiring a signal at a stop position. Alternatively, light irradiation and signal acquisition may be performed while continuously moving the supporter 400. According to this method, in addition to enabling scanning to be performed faster than when the supporter 400 is repetitively stopped and moved, there is also an advantage that disturbance of a liquid surface of the acoustic matching member 800 filling the supporter 400 can be more readily suppressed.

Step S400 is a step of acquiring functional information of the object E based on a received signal. The information processing unit 710 acquires functional information of the object E by applying a process based on an image reconstruction algorithm on the received signal acquired in S300. As the image reconstruction algorithm for acquiring functional information, a back projection method in a time domain or a Fourier domain which is commonly used in tomographic technology can be used. Moreover, when more time can be used for reconstruction, an inverse problem analysis method based on repetitive processing may be used. As described earlier, the received signal acquired in S300 is a received signal originating from the high sensitivity region G which is obtained by receiving, at high sensitivity, a photoacoustic wave generated inside the object E. Therefore, in the present step, functional information of the inside of the object E can be acquired with good accuracy or, in other words, with high resolution and quantitativity.

S500 is a step following the irradiation of light by the light source 100 of simultaneously photographing the object E with the camera units 600 and 610 and generating a captured image. At this point, favorably, the influence of light irradiated from the light source 100 on the captured image is reduced. Conceivable examples include a method of further delaying timing of photography, a method of inserting a filter for cutting a wavelength of the light source 100 into the lens of a camera unit, and a method of contrarily irradiating light after photography by a camera unit. In addition, a method may be used in which images at two locations 600 and 610 are simultaneously acquired using one camera. In other words, two images can be simultaneously photographed by providing lenses at two locations and using a mirror to collect and capture light into a single camera.

S600 is a step of acquiring positional information of the object E from a plurality of captured images. A method of calculating a distance of a characteristics point P with a stereoscopic method using two simultaneously photographed captured images will now be described.

Figure 7:
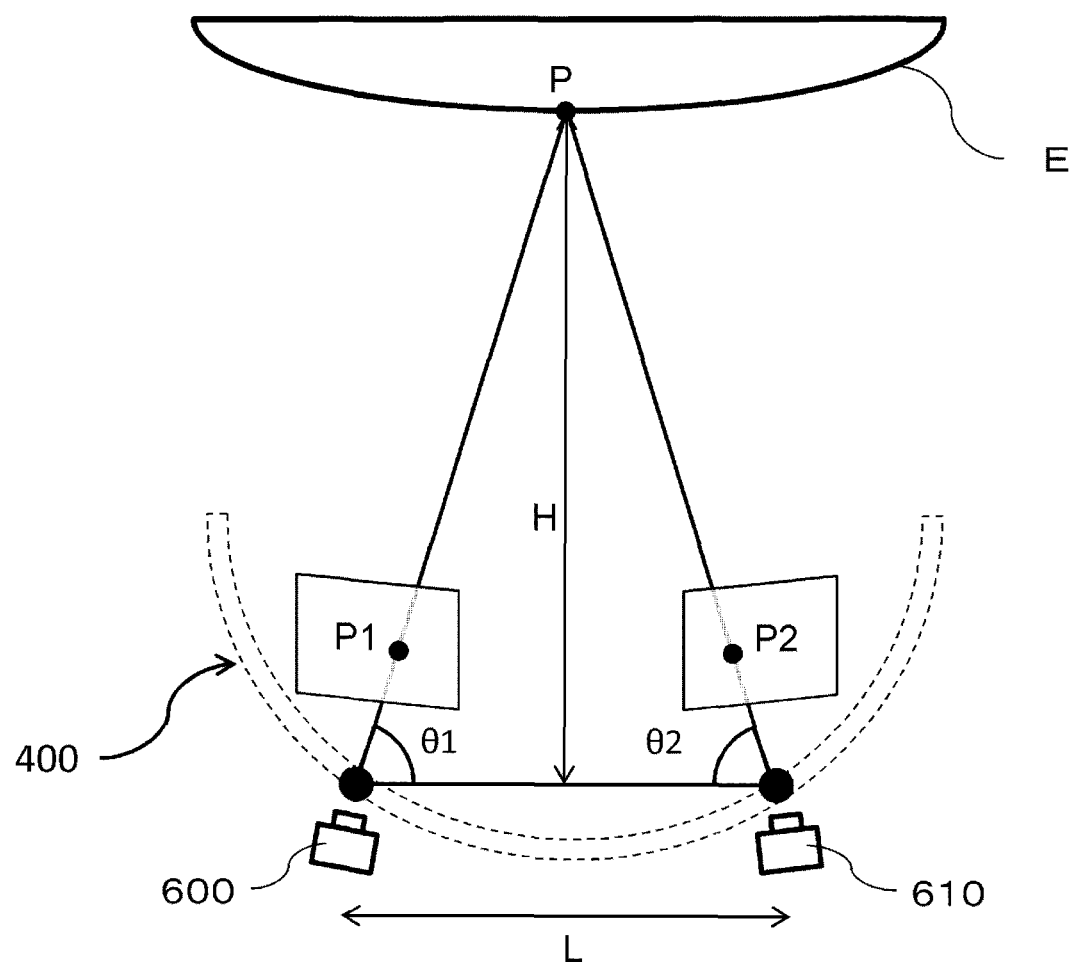
FIG. 7 is a diagram showing a method of calculating a distance of a characteristics point using a compound-eye camera.

Assuming that a positional relationship L of the respective camera units has been obtained as shown in FIG. 7, when an object is photographed using the two camera units, a relationship between a given characteristics point P on the object and an image projected onto a camera unit can be obtained by triangulation. In other words, an angle $\theta 1$ is calculated based on a coordinate P1 of a point where a characteristics point P of interest appears on the camera unit 600, and an angle $\theta 2$ is calculated based on a coordinate P2 of a point appearing on the camera unit 610. Therefore, based on the distance L between the two points and both end angles $\theta 1$ and $\theta 2$, a distance H between the two camera units and the characteristics point P can be acquired by the following equation.

[Math. 1]

$$H = (L*\tan\theta 1 * \tan\theta 2)/(\tan\theta 1 + \tan\theta 2) \qquad (1)$$
$$= (L*\sin\theta 1 * \sin\theta 2)/\sin(\theta 1 + \theta 2)$$

Therefore, since the object E can be photographed by two camera units prior to performing light irradiation and positional information of each characteristics point of the object E can be obtained, correspondence can be determined as positional information when a received signal of the object E is obtained.

S700 is a step of determining whether or not measurement in the movement region is to be repeated. A determination that measurement is to be repeated is made when a location not yet measured remains in the movement region. Subsequently, a relative positional relationship between the object and the supporter is changed by the scanner 500. As a result, the supporter 400 moves to the second measurement position within the set movement region and which differs from the first measurement position. In addition, when the supporter 400 is at the second measurement position, a similar step to the measurement at the first measurement position is performed and an electrical signal and a captured image at the second measurement position are acquired. On the other hand, when an electrical signal and a captured image of the object E have been acquired at all measurement positions within the movement region set in S200, a transition is made to a next step. At this point, desirably, with respect to positional information of the object E, a position acquired at the first measurement position is secured as a reference value and positions acquired at second and subsequent measurement positions are managed by adding or subtracting differences. In this case, the respective positions described as the first measurement position and the second measurement position may be regarded as a first relative position and a second relative position according to the present invention.

S800 is a step of associating positional information of the object E with measurement position information of the high sensitivity region G to acquire volume information of the object E. Measurement position information of the high sensitivity region G is positional information calculated based on shape information of the shape holding unit 1100 and information related to a movement region in the X, Y, and Z directions of the supporter 400. Moreover, measurement position information set by the information processing unit 710 is stored in the storage unit 720. The measurement position information represents a relative position of the supporter 400 and the shape holding unit 1100 and indicates that a position of the high sensitivity region G is moving in accordance with a scanning position of the supporter 400.

FIG. 8A is a diagram schematically showing a transition of movement of the high sensitivity region G in the XZ plane when the object E is fixed by the shape holding unit 1100 and there is no change to positional information. While the high sensitivity region G is depicted as though moving in a straight line in the X direction in the drawing, an actual movement direction is not limited thereto. The present diagram may also be considered a drawing which, for example, shows a spiral movement or a reciprocal movement of the high sensitivity region G converted into a rectilinear movement. The high sensitivity region G in the present practical example has a spherical shape. Photoacoustic measurement is performed and a captured image and a received signal of the object E are acquired at least once while the supporter 400 moves a distance equal to the radius of the high sensitivity region G. In addition, based on measurement position information (a0 to a8) stored in the storage unit 720, images are superimposed and volume information of the entire region of the object is acquired.

Moreover, the direction of superimposition is not limited to the movement direction (the X direction in FIGS. 8A and 8B). For example, when volume information is obtained as shown in FIG. 6, superimposition can be performed in a plurality of directions. A method of superimposition is arbitrary and for example, a method of simply averaging values of overlapping voxels or a method of weighting voxel values within a certain range around an object voxel may be used.

Next, FIG. 8B shows a schematic diagram of a transition of a position of the high sensitivity region G in the XZ plane when there is body motion of the object E. Although, actually, the high sensitivity region G does not move vertically but a portion of the object superimposed on the high sensitivity region moves vertically, the present diagram shows a vertical movement of volume information acquired from the high sensitivity region for the sake of convenience. In this case, superimposition must be performed by calculating a difference of the object E from a reference position. In consideration thereof, a position of the high sensitivity region G with respect to the object E is calculated from positional information of the object E obtained in S600 and measurement position information stored in the storage unit 720 and a position of superimposition on volume information is corrected. As described above, by performing volume superimposition after applying correction reflecting positional information in accordance with body motion, preferable information is obtained.

In FIG. 8B, a variation in position in the Z direction with respect to a reference position b0 is manifested as a difference from a reference position indicated by a dashed line. In addition, difference information of an object position is associated with measurement position information denoted by b1 to b8. Therefore, an information source used for volume superimposition can be changed in accordance with a vertical movement of the object E. As a superimposition method when there is a vertical movement of the object, data of a position slightly deviated from the high sensitivity region G can be used. For example, at b1 to b3 in FIG. 8B, the high sensitivity region G is below a height of a reference position. In other words, the object has conceivably been displaced upward in the Z direction.

Therefore, when imaging at the same height as b0 is desired, volume information upward in the Z direction than the high sensitivity region G may be used. On the other hand, since the object has conceivably been displaced downward in the Z direction at b5 and b6, volume information below the high sensitivity region G is used. Conversely, even though heights can no longer be aligned in the Z direction in information after superimposition, superimposition using volume information solely acquired in the high sensitivity region G can be performed. Even in this case, by also scanning the supporter 400 in the Z direction, a wide range of the object can be included in the high sensitivity region G.

According to the present practical example, by detecting positional information of the object and correcting a change in a relative position with respect to the high sensitivity region G, superimposition of volume information can be preferably performed and a specific information distribution of the object in a desired region can be accurately generated. As a result, a deviation of a measurement position of the object E due to body motion or the like can be reduced and imaging of a wide range of the object can be performed without causing a decline in resolution. In the present practical example, correction of a change in position of the object in the Z direction has been described. However, the method described above can also be applied to body motions in the X direction and the Y direction or to a body motion combining such body motions. The present invention is particularly effective when a shape of an object readily changes in accordance with body motion such as when a holding member of the object is not provided, when there is a gap between the object and the holding member, and when the holding member is constituted by a soft material such as a sheet member.

First Modification

Figure 5:
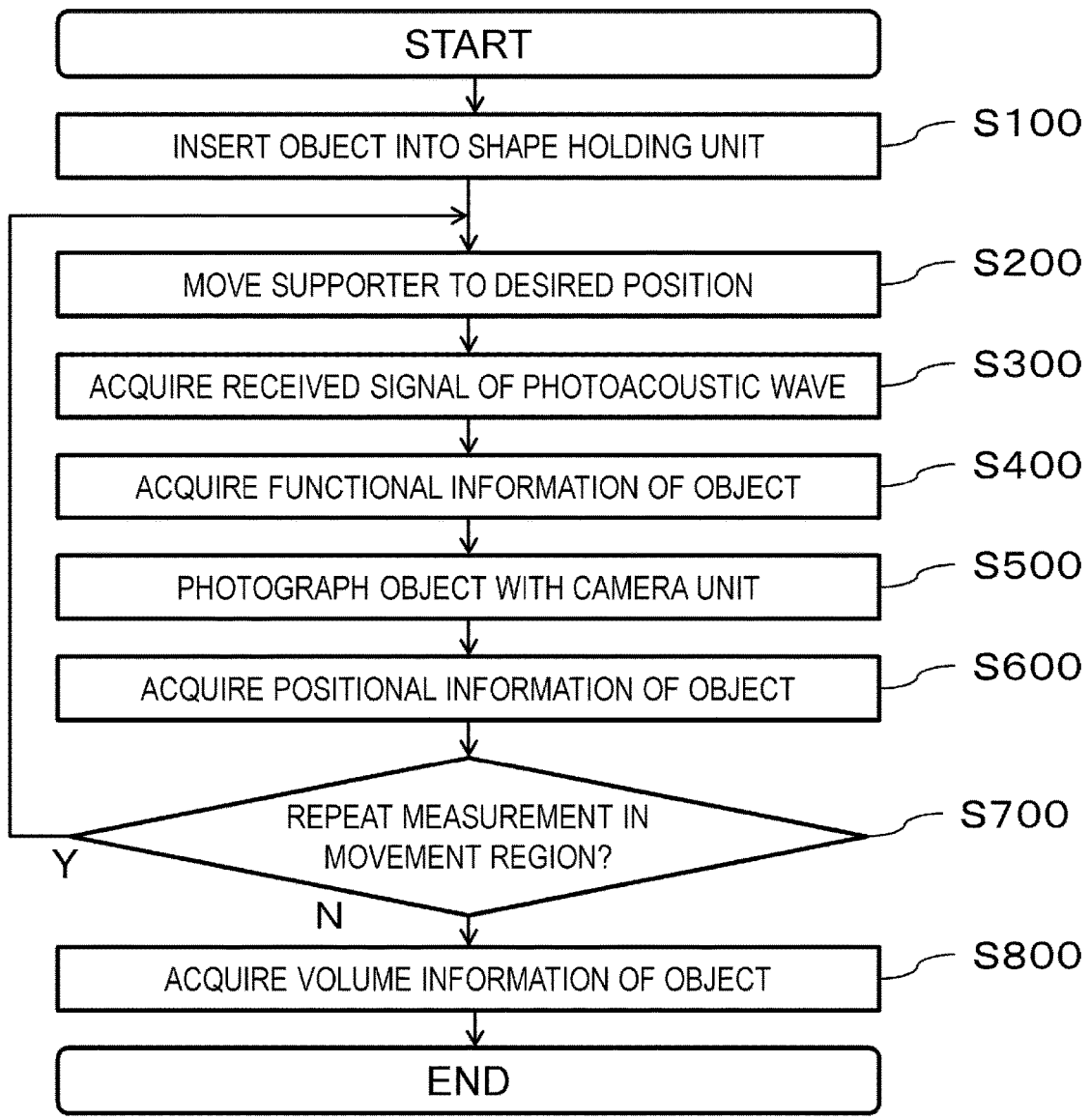
FIG. 5 is a diagram showing steps of acquiring positional information of an object of a photoacoustic apparatus according to a first practical example.

In the flow shown in FIG. 5, light irradiation and photoacoustic wave reception are performed for each measurement position to obtain volume information. In addition, a superimposition process is performed after scanning of an entire movement region is completed. However, depending on the performance of a camera or an information processing apparatus, the presence or absence or a degree of body motion can be detected for each measurement position. In this case, depending on the performance of the scanner, an influence of body motion may be corrected at a next measurement position and a supporter may be moved so that the high sensitivity region G is formed at a desired position.

Second Modification

The present invention is not limited to cases where conversion elements with mutually different directional axes are arranged on a hemispherical supporter so as to form a high sensitivity region. The present invention is preferably used in a case where a shape of an object readily changes in accordance with body motion and the conversion elements and the object are arranged at a distance via an acoustic matching member or the like. For example, a method according to the present invention using positional information can even be applied when a single-element probe, a 1D linear probe, or a 2D planar probe is used as the supporter.

Second Practical Example

In the first practical example, a stereoscopic method using images photographed with two cameras is described as steps for acquiring positional information of the object E. In the present practical example, a camera movement method in which photography is performed by moving a monocular camera will be described.

Figure 9:
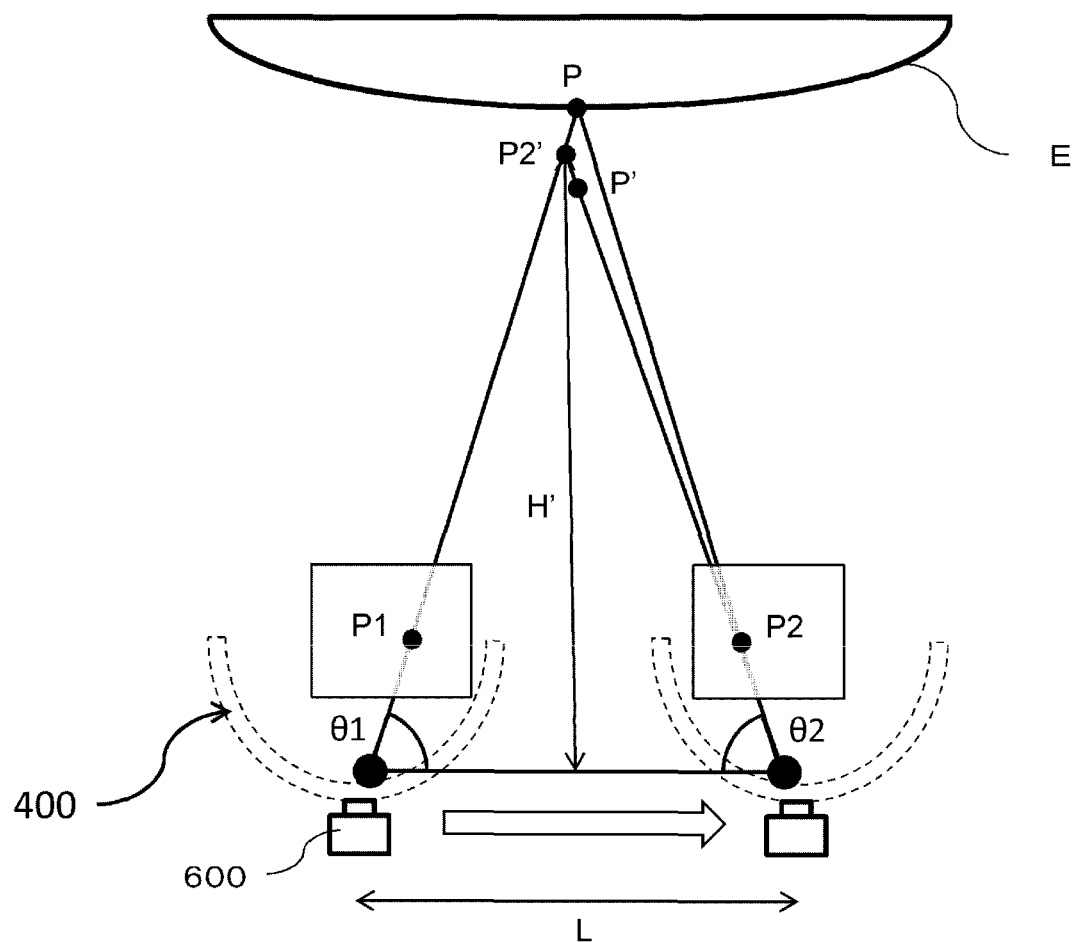
FIG. 9 is a diagram showing a method of calculating a distance of a characteristics point using a monocular camera according to a second practical example.

In a similar manner to the first practical example in which photography is simultaneously performed using two cameras, positional information can also be acquired using a stereoscopic method in the camera movement method in which a monocular camera is moved and photography is performed at different positions. A description will now be given using the camera 600 shown in FIG. 9 and an arrangement of a characteristics point P. First, the camera 600 photographs the characteristics point P at a left-side position to obtain a first image. Next, the camera is moved by a distance L and photography is performed at a right-side position to obtain a second image. Subsequently, using the first image and the second image, a distance H can be calculated by triangulation based on a relationship between the characteristics point P on the object and an image projected on the camera unit.

However, when the characteristics point P moves to P' during a period of time T2 in which the camera moves by the distance L, since a distance H' measured by triangulation becomes an intersection of the characteristics point P observed from the left-side point and the characteristics point P' observed from the right-side point, a value that differs from the actual distance H is obtained. Therefore, a ratio of the period of time T2 required for movement of the camera must be sufficiently small with respect to a period 1/T1 of positional variation of the object E (T1>>T2 must be satisfied).

As described above, even with a simple configuration, the object information acquiring apparatus according to the present practical example can detect positional information of an object and correct a deviation of the position of the high sensitivity region G. As a result, volume information of the object in a desired region can be acquired with high accuracy.

Third Practical Example

In the first and second practical examples, a stereoscopic method that is an example of passive measurement is described as steps for acquiring positional information of the object E. In the present practical example, active measurement in which the object E that is a measurement object is irradiated with specific light, a radio wave, and the like for assisting measurement will be described.

Active measurement refers to a method in which the object E that is a measurement object is irradiated with light, a radio wave, a sonic wave, or the like for three-dimensional measurement and measurement is performed using information thereof. For example, an "optical radar method", an "active stereo method", and an "illuminance difference stereo method" are known. The "optical radar method" refers to a method in which a distance image is obtained based on the time required by light, a radio wave, an ultrasonic wave, or the like to bounce back from an object. The "active stereo method" refers to a method in which measurement is performed by, instead of using two cameras, replacing one of the cameras with an apparatus that projects light and is further classified into various methods according to types of projected light. The "illuminance difference stereo method" refers to a method in which a plurality of light sources are used with respect to an object that is a measurement object and a direction of a surface is obtained based on a plurality of images photographed while switching among the light sources. Since pixels on a surface of the object close to a light source appear brightly to enable an incline to be measured in a light source direction, a solid can be measured by obtaining a plurality of such inclines.

Various methods of the "active stereo method" can be classified into a spotlight projection method, a slit light projection method (a light cutting method), a pattern light projection method, and the like. The slit light projection method refers to a method in which photography is performed in a state where slit light is projected on an object and measurement is performed by extracting a degree of change in the light, and a light cutting image by one slit is obtained by one photography session. The pattern light projection method refers to a method in which a single projection pattern (for example, a large square pattern scattered with random dots) is constantly projected on an object surface and an amount of movement at each location in the pattern is discerned by image processing from a captured image obtained by photography.

Figure 10:
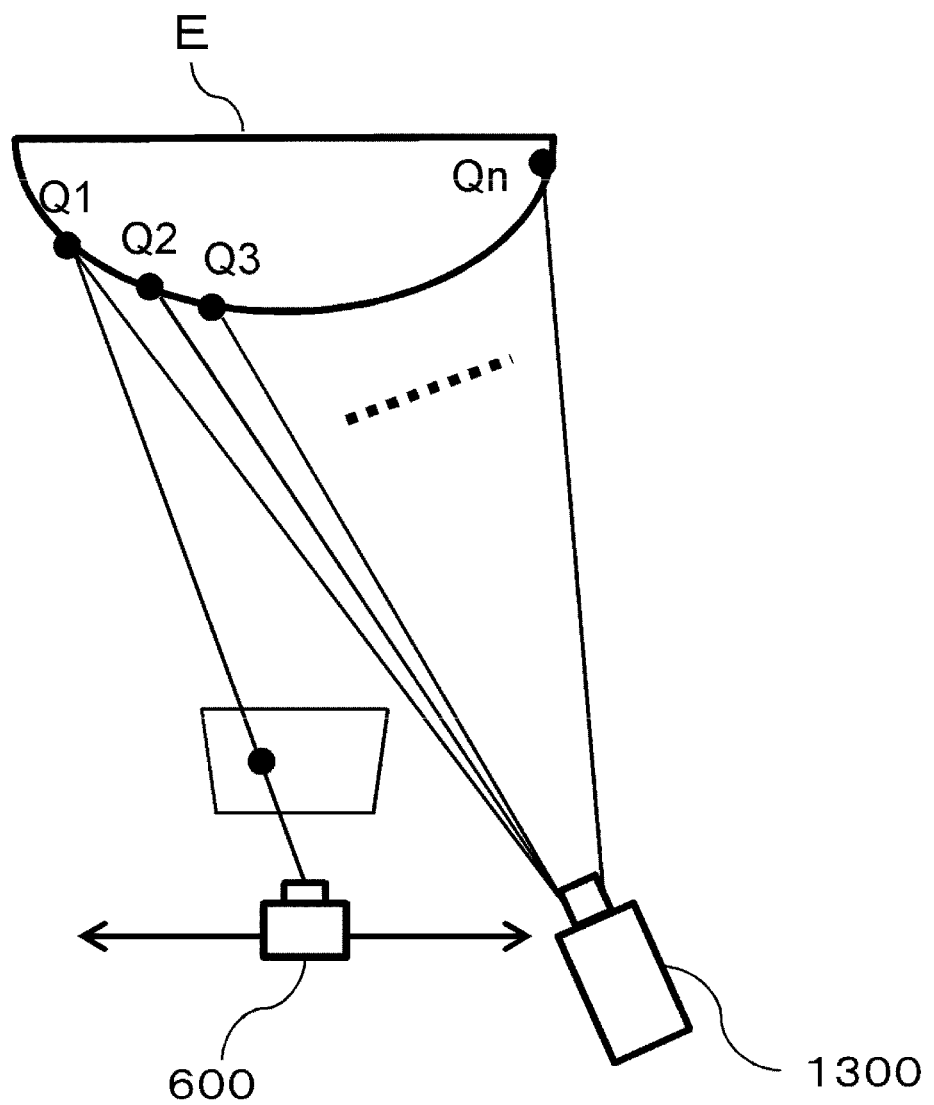
FIG. 10 is a diagram showing a configuration of a pattern light projection method using a monocular camera according to a third practical example.

In the present practical example, the pattern light projection method which is one "active stereo method" which exemplifies active measurement will be described. FIG. 10 is a configuration diagram showing triangulation applied to the present practical example by the pattern light projection method. This method is also based on triangulation. Specifically, pattern light Q1 to Qn is projected in a constant direction from a pattern light projection apparatus 1300 at a position set in advance with respect to the object E and the pattern light appearing on the object E is photographed by the camera 600 installed at another position. At this point, based on positions of the pattern light Q1 to Qn portrayed in captured images of the camera 600, a distance to the object is obtained using the principle of triangulation based on the position of the pattern light projection apparatus 1300 and the position of the camera 600. Extracting a characteristics point using pattern light is effective even with respect to an object having a surface without a characteristics point such as a breast.

While the camera 600 mounted to the supporter 400 is configured to move to an arbitrary position with respect to the object E in the present practical example, the pattern light projection apparatus 1300 is desirably fixed at a same position with respect to the object E. Specifically, when measuring positional variation while constantly irradiating a same position (a characteristics point) of the object E with the pattern light Q1 to Qn, the position of the pattern light projection apparatus 1300 must be fixed and an installation location thereof is to be a position separated from the supporter 400 and the scanner 500. However, when a three-dimensional shape of the object E is measured in addition to measuring positional variation with respect to a characteristics point on the surface of the object E, the camera 600 and the pattern light projection apparatus 1300 can be installed and operated on the same supporter 400.

As described above, by detecting positional information of an object and correcting a deviation of the position of the high sensitivity region G, the object information acquiring apparatus according to the present practical example has an effect of preventing a decline in resolution of volume information of the object in a desired region.

Fourth Practical Example

In the above practical examples, an example has been described where a relative position of the supporter 400 with respect to an object is varied and, based on a received signal acquired at each relative position, functional information of the object E is acquired. In other words, functional information of the object E is acquired based on a received signal obtained by one laser irradiation. According to this method, by performing signal processing according to an image reconstruction algorithm on a received signal obtained from the high sensitivity region G for each laser irradiation timing, functional information of the high sensitivity region G conforming to motion of the supporter 400 can be generated every time. Therefore, the method is suitable for a configuration in which, for example, functional information is viewed with a monitor by sequential processing (real-time processing) while moving the supporter. In other words, as scanning of the supporter 400 progresses, functional information of scanned locations can be sequentially updated.

In contrast, in the present fourth practical example, functional information of the object E is acquired based on a received signal obtained by a plurality of laser irradiations. This method is preferably used in, for example, a process where time constraint on signal processing is not strict and signal processing is collectively performed. In the present practical example, such a process is referred to as an offline process. In the first practical example, position of volume data obtained by computational processing is corrected and volume data are superimposed on each other. The present practical example differs from the first practical example in that computational processing is performed after correcting a position in a received signal and volume data is then generated. With the method according to the present practical example, a deviation of a position due to movement of an object can be corrected with higher accuracy. An apparatus configuration according to the present practical example may be similar to the configurations of the practical examples described above.

Figure 11:
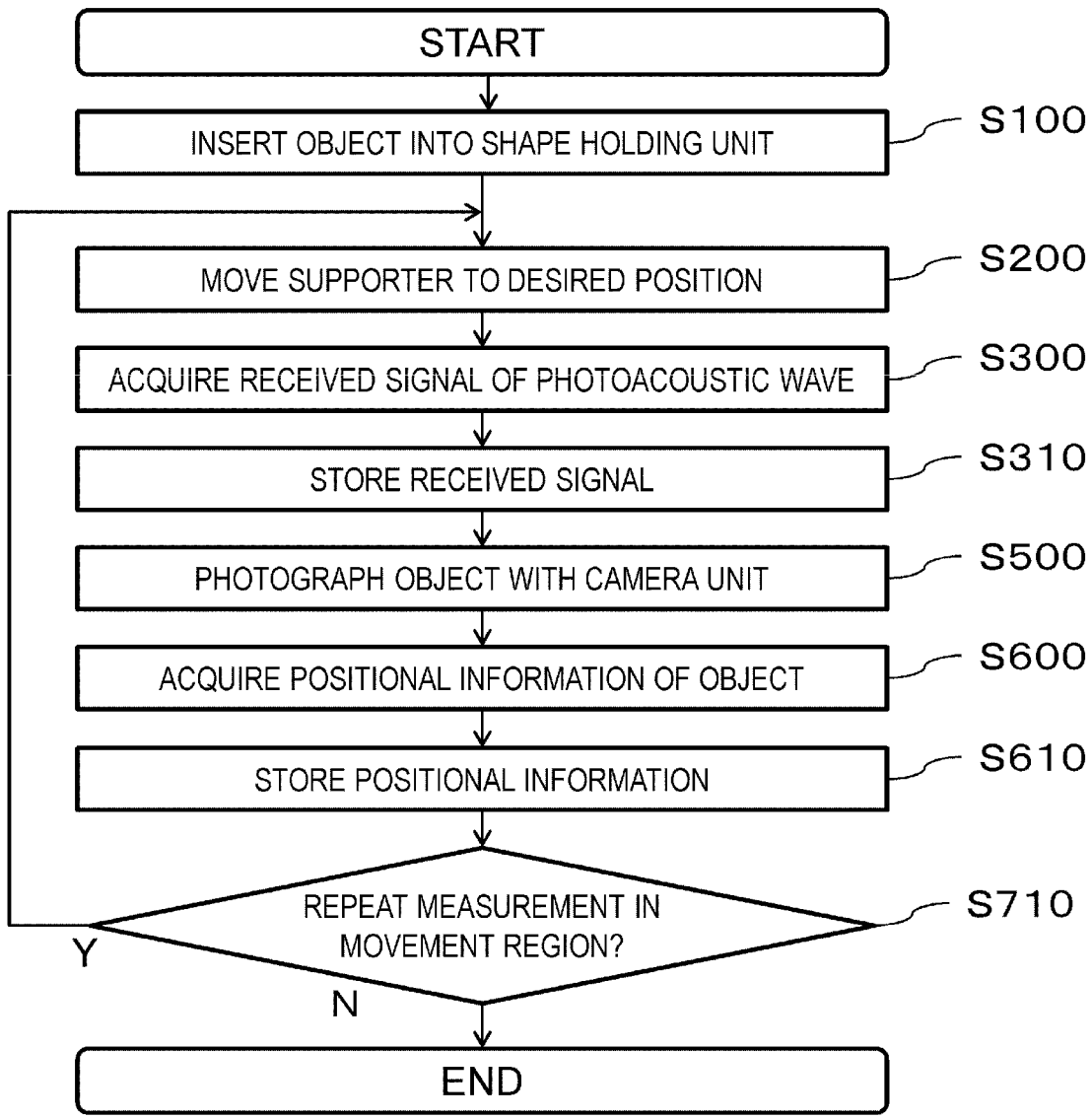
FIG. 11 is a diagram showing steps of acquiring information of an object according to a fourth practical example.

FIG. 11 is a flow chart showing an example of a signal acquisition flow of an offline process according to the present practical example. Since the steps of acquiring a received signal from S100 to S300 are similar to the processes shown in FIG. 5, a description thereof will be omitted. In the present practical example, after step S300, a process of step S310 is performed instead of step S400.

In step S310, the received signal acquired in step S300 is stored in the storage unit 720. Unlike step S400 in the first practical example, functional information need not be acquired at this point.

Since processes of steps S500 and S600 are similar to the processes shown in FIG. 5, a description thereof will be omitted.

In the present practical example, a process of step S610 is performed after step S600. In step S610, positional information of the object is stored in the storage unit 720.

Subsequently, in step S710, a determination on whether or not measurement is to be repeated in the movement region is made, and when measurement is not completed in the movement region, a return is made to step S200. When a determination of not repeating measurement in the movement region is made, the measurement is concluded.

After measurement is finished, the information processing apparatus 700 executes an offline process using signals stored in the storage unit 720 in the repetitively-executed steps S310 and S610.

Figure 12:
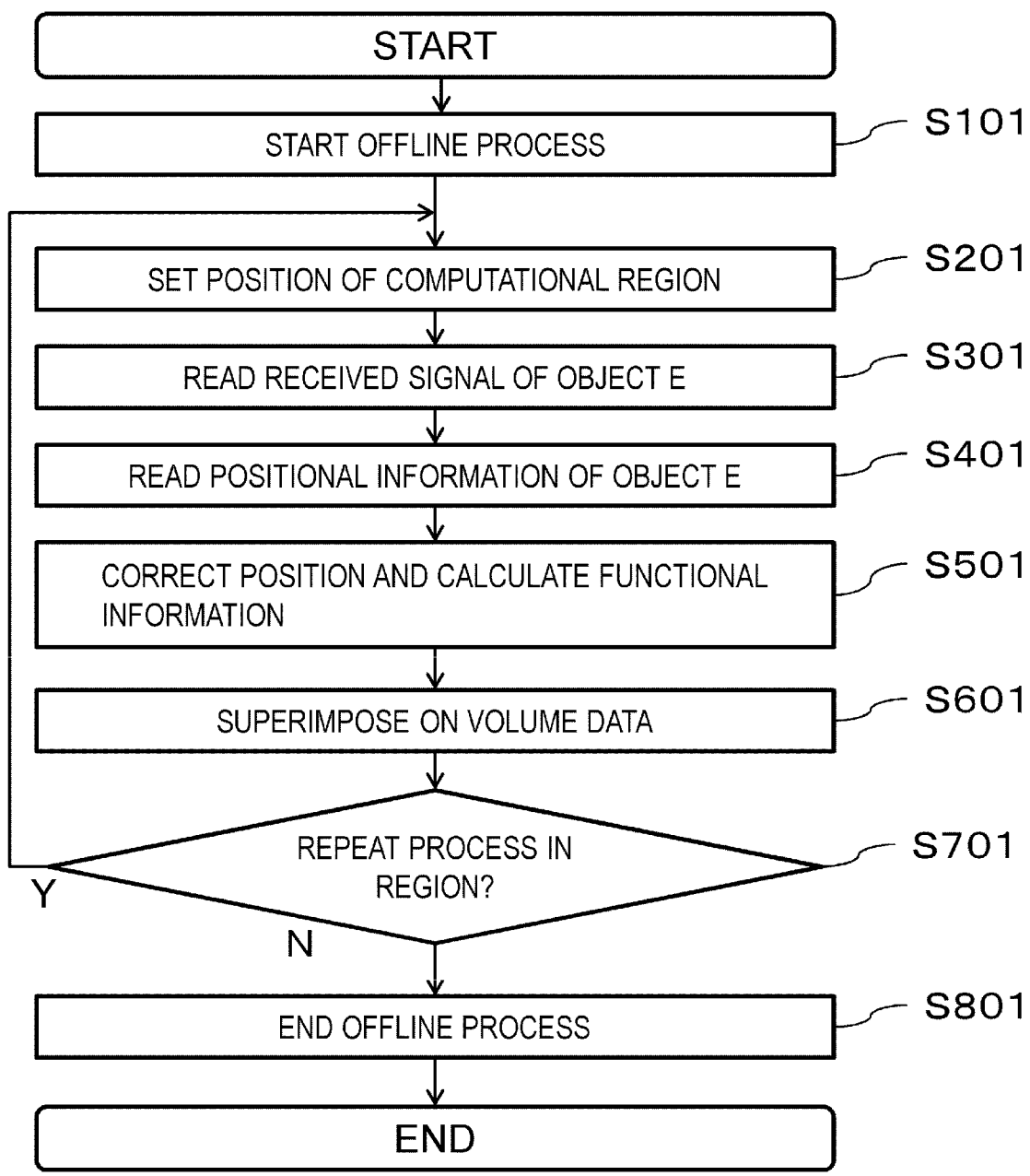
FIG. 12 is a diagram showing steps of an offline process according to the fourth practical example.

FIG. 12 is a flow chart showing an example of a signal processing flow of an offline process according to the present practical example. A case where signal processing is performed by the information processing apparatus 700 will be described in the present practical example. However, signal processing is not limited to being performed by the information processing apparatus 700 provided in the photoacoustic apparatus and may instead be performed by a computer provided separately from the photoacoustic apparatus. Using a computer mounted with a plurality of GPUs is advantageous in increasing processing speed.

A process until volume data is generated using a received signal based on an acoustic wave propagated from the object E and positional information stored in accordance with the flow shown in FIG. 11 will be described. A range in which volume data is generated may be specified by a user via the input unit or may be specified by the information processing apparatus 700 based on a prescribed determination.

In step S101, an offline process of the specified range is started.

Step S201 is a step of determining a prescribed position of a computational region to be computed according to an image reconstruction algorithm.

In step S301, received signals of a plurality of measurement locations necessary for signal processing are read with respect to the prescribed position determined in step S201. In step S401, positional information of the object E when acquiring the plurality of received signals is read.

Step S501 is a step of processing the received signals and calculating functional information in the computational region. By simultaneously correcting a deviation of the position of the object E at the time of measurement of the received signals in this step, a positional error in signal processing can be reduced. A specific example of correcting a deviation of a position is a method of correcting sound velocity in consideration of an interface between the object E and the shape holding unit 1100 or the acoustic matching member.

Figure 13:
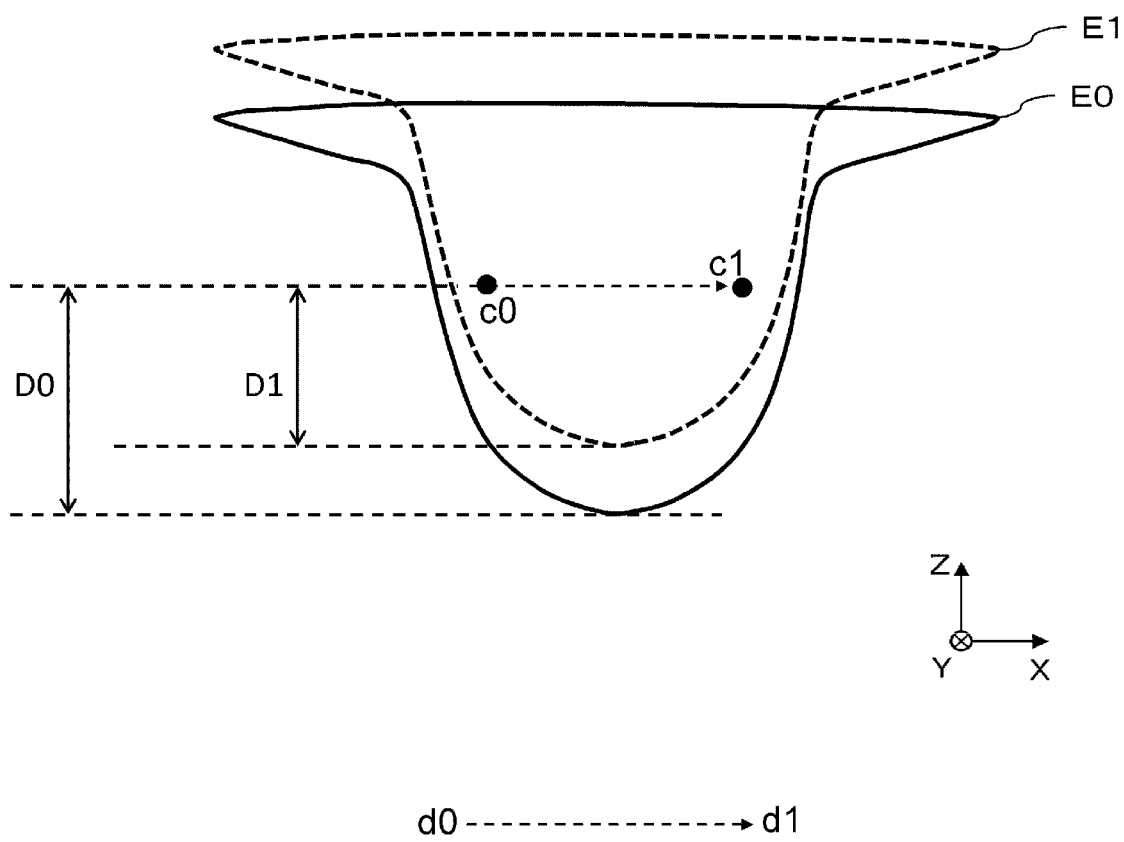
FIG. 13 is a diagram illustrating position correction according to the fourth practical example.

FIG. 13 is a diagram illustrating correction of position in S501 and shows a change in position from timing t0 to timing t1. Reference characters d0 and d1 respectively denote probe positions at the timings t0 and t1. When there are a plurality of conversion elements 300, a center of a hemispherical surface may be assumed to be a probe position. Reference characters c0 and c1 respectively denote positions of a center of the high sensitivity region G at the timings t0 and t1. In addition, reference characters E0 and E1 indicate a deviation of object positions due to body motion between the timings t0 and t1.

As the probe position moves in parallel from d0 to d1, the center point of the high sensitivity region G also moves in parallel from c0 to c1. In this case, at the timing t0, the point c0 is positioned at a depth of D0 from a tip of the object. On the other hand, since the object has moved in a positive direction of a z axis due to body motion, at the timing t1, the point c1 is positioned at a depth of D1 from the tip of the object. In other words, due to body motion, the high sensitivity region has moved to a shallower position of the object. Generally, since sound velocity of an acoustic matching liquid is higher than sound velocity of a living organism, the period of time until an acoustic signal is propagated differs between timings t1 and t2. As a result, an inappropriate electrical signal ends up being extracted during image reconstruction and causes a decline in calculation accuracy of functional information.

In addition, a variation in the position of the object E becomes an influencing factor with respect to a delay time in received signals, a variation in sensitivity attributable to the directionality of conversion elements, a variation in a passage distance through the acoustic matching member 800 that fills the space from the conversion elements to the object E, and the like. These influences will now be considered. First, with respect to variation in sensitivity, signal gain can be adjusted. In addition, with respect to a passage distance through the acoustic matching member 800, a correction can be made when a distance of body motion is obtained since respective distances of a living organism portion and an acoustic matching liquid portion on a route of an acoustic wave can be acquired.

In step S601, volume data is generated by superimposing functional information at a prescribed position. Step S701 is a step of determining whether or not computational processing in the specified range is to be repeated. When it is determined that computational processing in the specified range has not been completed, a return is made to step S201 and the process is repeated. When it is determined that computational processing in the specified range has been completed, the flow advances to step S801. The offline process is finished in step S801 and volume data of the specified range is output. The volume data is displayed on the display 900 as an image or stored in the storage unit 720.

Moreover, the computational region set in a specified range is not limited to a region along a spiral shape shown in FIG. 6 during data acquisition. For example, the computational region may be constituted by squares perpendicular to the XY direction or by a plurality of circles with different radii.

According to the present practical example, when correcting positions of a plurality of received signals and performing signal processing according to an image reconstruction algorithm, at least one parameter of a delay time until an acoustic wave reaches each conversion element from a target point inside an object, sensitivity of the conversion element, and sound velocity can be corrected. As a result, accuracy of generated functional information is improved.

Fifth Practical Example

Another practical example of the present invention will now be described. In the present practical example, an object information acquiring apparatus can selectively execute two modes. A first mode is a mode in which, as described in the first practical example, volume data generated from an electrical signal obtained based on one light irradiation is corrected based on positional information. A second mode is a mode in which, as described in the fourth practical example, volume data is generated while electrical signals obtained at a plurality of relative positions are corrected based on positional information.

By performing an operation in the first mode, the object information acquiring apparatus according to the present practical example updates, whenever necessary, an image of volume data in which a deviation of a position of an object has been corrected while performing photoacoustic measurement. Once measurement of a specified measurement range is finished, an operation in the second mode is performed. Specifically, with respect to received signals stored in the storage unit through the operation in the first mode, a deviation of a position is corrected based on positional information of the object E when each received signal had been obtained and volume data is obtained. The volume data obtained in this manner is displayed on a display unit.

According to the present practical example, an operator of the object information acquiring apparatus can check functional information in real time even when a measurement is being performed and can check an image in which a deviation of a position has been corrected with higher accuracy after the measurement is completed. As a result, a highly convenient apparatus for an operator can be realized.

The present invention can also be realized by executing the processing described below. Specifically, the present invention can also be realized by supplying a program that realizes one or more functions of the embodiment described above to a system or an apparatus via a network or various storage media and having one or more processors in an information processing apparatus in the system or the apparatus read and execute the program. Alternatively, the present invention can also be realized by a circuit (for example, an FPGA or an ASIC) which realizes one or more functions.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-162132, filed on Aug. 19, 2015, and, Japanese Patent Application No. 2016-116259, filed on Jun. 10, 2016, which are hereby incorporated by reference herein in their entirety.

What is claimed is:

1. An object information acquiring apparatus comprising:
a light source which generates light;
a plurality of conversion elements, each receiving an acoustic wave generated when an object is irradiated with the light and outputting an electrical signal;
a supporter which supports the plurality of conversion elements; and
an imager including a plurality of optical cameras, which is arranged on the supporter and which acquires an optical image of the object,
wherein the supporter has a hemisphere shape and supports the plurality of conversion elements along a plurality of spiral arrays on the hemisphere shape,
wherein the plurality of optical cameras is arranged at a region other than the plurality of spiral arrays on the hemisphere shape, and
wherein the plurality of optical cameras is arranged at a diagonal position with respect to a pole of the hemisphere shape.

2. The object information acquiring apparatus according to claim 1 further comprising:
a scanner which changes a relative position between the object and the supporter;
a specific information acquirer which acquires a first photoacoustic image of the inside of the object based on the electrical signal acquired at a first relative position between the object and the supporter, and which acquires a second photoacoustic image of the inside of the object based on the electrical signal acquired at a second relative position between the object and the supporter that differs from the first relative position; and
a positional information acquirer which acquires positional information of the object at the first and second relative positions on the basis of optical images acquired by the imager at the first and second relative positions.

3. The object information acquiring apparatus according to claim 1, wherein the supporter stores an acoustic matching liquid in such a manner that the acoustic matching liquid is arranged between the supporter and the object.

4. The object information acquiring apparatus according to claim 2, wherein the positional information acquirer acquires the positional information by comparing a characteristics point of the object between the images respectively obtained at a plurality of the relative positions.

5. The object information acquiring apparatus according to claim 4, wherein the characteristics point is a marker, or a characteristic structure of the object.

6. The object information acquiring apparatus according to claim 2, wherein the plurality of conversion elements are arranged on the supporter so that a high sensitivity region is formed in a region in which directions of high receiving sensitivity of at least a part of the conversion elements converge, and
the specific information acquirer acquires the first and second photoacoustic images in a region including the high sensitivity region with respect to the respective relative positions.

7. The object information acquiring apparatus according to claim 1 further comprising:
a scanner which performs scanning that changes a relative position between the object and the supporter;
a positional information acquirer which acquires, at a plurality of the relative positions during the scanning, positional information of the object based on the optical image acquired by the imager; and
a specific information acquirer which acquires a photoacoustic image of the inside of the object based on the electrical signal and the positional information.

8. The object information acquiring apparatus according to claim 2, wherein the object information acquiring apparatus is capable of operating in a first mode in which correction is performed on the electrical signals obtained at the plurality of relative positions.

9. The object information acquiring apparatus according to claim 8, wherein the correction of the electrical signal is correction of at least one parameter among a delay time of the acoustic wave, sensitivity of the conversion elements, and sound velocity of the acoustic wave.

10. The object information acquiring apparatus according to claim 1, wherein the supporter supports the plurality of conversion elements at equal intervals along the plurality of spiral arrays.

11. The object information acquiring apparatus according to claim 3, further comprising:
an optical system which irradiates the object with the light;
a hole which supplies and discharges the acoustic matching liquid supply and discharge; and
a temperature sensor which monitors temperature of the acoustic matching liquid,
wherein the supporter supports the optical system at a pole of the hemisphere shape, and
wherein the supporter supports the plurality of conversion elements, the hole, and the temperature sensor at regions other than the plurality of spiral arrays on the hemisphere shape.

12. The object information acquiring apparatus according to claim 1, wherein the number of the plurality of spiral arrays is four.

* * * * *